though the acetone peroxides are hazardous and explosive compounds when
United States Patent [19]

Costantini

[11] Patent Number: 5,003,109
[45] Date of Patent: Mar. 26, 1991

[54] DESTRUCTION OF ACETONE PEROXIDES

[75] Inventor: Michel Costantini, Lyon, France

[73] Assignee: Rhone-Poulenc Chimie, Courbevoie, France

[21] Appl. No.: 421,939

[22] Filed: Oct. 16, 1989

[30] Foreign Application Priority Data

Oct. 14, 1988 [FR] France .................. 88 14360

[51] Int. Cl.$^5$ .............................................. C07C 45/53
[52] U.S. Cl. ................................... 568/385; 568/798; 568/768
[58] Field of Search ................ 568/385, 411, 798, 768

[56] References Cited

U.S. PATENT DOCUMENTS 3,161,685 12/1964 Minisci ........................... 568/385

FOREIGN PATENT DOCUMENTS

| 637653 | 9/1963 | Belgium ........................... 568/385 |
| 0018803 | 11/1980 | European Pat. Off. ............ 568/385 |
| 286408 | 10/1988 | European Pat. Off. ............ 568/385 |
| 2165027 | 7/1972 | Fed. Rep. of Germany ...... 568/385 |
| 55-73796 | 6/1980 | Japan ................................. 568/385 |

OTHER PUBLICATIONS

World Patent Index Database Accession No. 80-50775 C, Semaine 29, Sections E14, J01, 1980; Derwent Publications Ltd., Londres, GB; & JP-A-55 73796 (Mitsui), 03-06-1980.
World Patent Index Database IBIO No. d'Accession 80-50774 C, Semaine 41, Sections E14, J01, 1980, Derwent Publications Ltd., Londres, G.B.; & JP-A-55 73795 (Mitsui), 03-06-1980.
World Patent Index Database No. d'Accession 83-788014, Semaine 41, Sections A41, D15, E19, 1983, Derwent Publications Ltd., Londres, GB; & SU-A-981247 (Cherevin) 15-12-1982.

*Primary Examiner*—James H. Reamer
*Attorney, Agent, or Firm*—Burns, Doane, Swecker & Mathis

[57] ABSTRACT

The acetone peroxides contained in oxidate reaction mixtures thereof, e.g., those resulting from phenol syntheses, are hazardous and explosive compounds when present in the solid state, and are consumed by (a) adjusting the pH of such reaction mixture to a value ranging from 4 to 8; (b) adding a copper compound to such reaction mixture; and (c) maintaining such reaction mixture at a temperature ranging from 50° C. to 150° C.

15 Claims, No Drawings

DESTRUCTION OF ACETONE PEROXIDES

BACKGROUND OF THE INVENTION

1. Field of the Invention

The present invention relates to the destruction of acetone peroxides, and, more especially, to the destruction of by-product acetone peroxides present in various reaction mixtures.

2. Description of the Prior Art

In certain known processes, particularly for the preparation of phenols and diphenols, acetone is contacted with an oxidizing agent such as hydrogen peroxide and the acetone peroxides are formed as by-products.

Thus, in the industrial synthesis of phenol from cumene, acetone and its by-products such as 2-phenyl-2-propanol are formed to a certain extent from the final product phenol. It has long been sought to enhance the phenol productivity of the process, in particular by oxidizing the 2-phenyl-2-propanol to cumenyl hydroperoxide, which itself splits into phenol + acetone. This oxidation may be carried out by the addition of hydrogen peroxide to the reaction mixture, as described in FR 1,077,475, to form acetone peroxides.

In the same manner, in the process for the preparation of hydroquinone from diisopropylbenzene described in EP-A-21,848, the productivity is again improved by the addition of hydrogen peroxide in order to oxidize certain by-products to diisopropylbenzene bis(hydroperoxide). This results in, as above, the formation of acetone peroxides in the reaction medium.

Another such process in which acetone peroxides are formed entails the hydroxylation of phenol, of substituted phenols or of phenol ethers, by hydrogen peroxide, in an acetone medium and in the presence of synthetic zeolites, described in the French Patent published under number 2,523,575. This process permits the preparation of diphenols, substituted diphenols or substituted phenols. However, during distillation of the acetone formed during the reaction or employed as solvent, and the distillation of the final product phenol or diphenols, the acetone peroxides produced by reaction between the oxidizing agent, such as hydrogen peroxide, and the acetone are either partly concentrated in the distillation residue, or partly entrained, and can crystallize in different elements of the apparatus.

Therefore, a potentially serious risk of explosion exists.

SUMMARY OF THE INVENTION

Accordingly, a major object of the present invention is the provision of a process for the destruction of the acetone peroxide by-products in a reaction mixture, before an optional distillation of one or more of the constituents of such mixture, and whereby any risk of explosion of the reaction mixture is conspicuously avoided.

Briefly, the present invention features a process for the destruction of the acetone peroxide by-products present in a reaction mixture, notably the reaction mixture resulting from the synthesis of phenol, diphenols or phenol derivatives, comprising (a) adjusting the pH of the reaction mixture to a value ranging from 4 to 8; (b) adding an effective amount of a copper compound such mixture; and (c) maintaining such reaction mixture at a temperature ranging from 50° C. to 150° C.

DETAILED DESCRIPTION OF THE PREFERRED EMBODIMENTS OF THE INVENTION

More particularly according to the present invention, the order in which the phases of the process are carried out may vary widely, namely:

(i) addition of the copper compound, then adjustment of pH and heating;

(ii) adjustment of pH, heating, then addition of the copper compound;

(iii) adjustment of pH, addition of the copper compound, then heating.

The acetone peroxides principally include two compounds, i.e., the dimer formed from 2 molecules of acetone, and the trimer formed from 3 molecules of acetone.

In a medium essentially constituted of phenol or diphenols, acetone, a minor amount of water and various by-products in relatively small quantities, the measurement of a pH is scarcely possible and is not significant.

Therefore, as utilized herein, the term pH will be used while describing the conditions under which it is measured.

The pH of the reaction mixture will be defined as the pH which is measured in an artificial mixture formed from 2 $cm^3$ of the said reaction mixture and 10 $cm^3$ of water.

All indications of pH given herein will therefore correspond to values determined as indicated above, without the particular procedure being specified each time.

The best results are obtained when operating at a pH ranging from 5 to 7.

The different processes for the formation of acetone peroxides are carried out in the presence of an acid catalyst.

For those processes entailing homogenous acid catalysis, the adjustment of the pH of the reaction mixture to the values indicated above will therefore generally be carried out by neutralization of the acidity of said reaction mixture.

Such neutralization can be carried out according to any known method which is conventional in this art.

In practice, a very simple technique is to use, for example, an aqueous solution of caustic soda.

For those processes entailing heterogeneous acid catalysis (titanium silicalite for example), adjustment of the pH will be carried out using an acid solution.

The copper compounds which are added according to the process of the invention are the cuprous or cupric compounds which are at least partially soluble in the reaction mixture to be treated.

In consideration of the oxidizing nature of the medium, the copper will essentially be in the cupric form, whatever the degree of oxidation in which it was introduced. For this reason, the following description will be confined to cupric compounds.

Exemplary copper compounds which are at least partially soluble in the mixture to be treated are the cupric carboxylates such as, for example, cupric acetate, cupric propionate, cupric hexanoate, cupric octanoate and cupric benzoate and the cupric halides, such as cupric chloride. In certain cases, the presence of water in the reaction medium will permit other copper salts to be used, such as copper sulfate or copper nitrate.

Copper acetate is very particularly suitable.

If, as is most often the case, the pH adjustment of the reaction mixture to be treated is carried out before addition of the cupric compound, the salt formed during neutralization of the acidity of the mixture may be separated, by filtration for example, before introducing the cupric compound.

The amount of cupric compound which is added in the present process can vary over wide limits.

Normally, from 0.05 to 5 moles of cupric compound are added per 1 mole of acetone peroxide Preferably, the cupric compound acetone peroxides molar ratio will range from 0.1 to 2.

The temperature at which the destruction of the acetone peroxides is accomplished preferably ranges from 60° C. to 130° C.

Generally, in order to avoid distillation of the most volatile compounds in the reaction mixture to be treated, the process will be carried out in a closed reactor, and therefore under the autogenous pressure of the different reagents.

The duration of the treatment depends on the temperature. It can vary from a few minutes to about 10 hours. These treatment times are not, in themselves, critical, since they depend on the temperature and on the acetone peroxide content.

The two acetone peroxides can, in any event, behave differently.

The dimer is destroyed by the action of cupric compounds, even at relatively low temperatures, as long as the operation is carried out at a pH from 4 to 8. The destruction of the trimer requires either the use of the aforementioned conditions of temperature, a pH ranging from 4 to 8 and the presence of a cupric compound, or heating at an acid pH (less than 4) in the presence or absence of a copper compound.

Therefore, it is the combination of the different parameters of the process (temperature, pH, cupric compound) which effects conversion of all of the acetone peroxides.

The difference in the behavior of the two acetone peroxides indicated that the process can be carried out:

(i) either in a single stage, during which the reaction mixture to be treated is adjusted to the required pH, the cupric compound is added and the temperature of the mixture is adjusted to the selected temperature; or (ii) in two successive stages, entailing first heating the reaction mixture to be treated at a pH of less than 4, for a few minutes to a few hours, in the presence or absence of the copper compound, then adjusting the pH to the required value of 4 to 8 after cooling the reaction mixture and optional addition of the copper compound, if it has not already been introduced, and lastly resuming heating to the same temperature as above or to a higher temperature.

The reaction mixture treated by the process according to the invention may then be subjected to the different separation phases which are typical for the products which it contains, for example distillation or recrystallization.

In order to further illustrate the present invention and the advantages thereof, the following specific examples are given, it being understood that same are intended only as illustrative and in nowise limitative.

EXAMPLE 1

Preparation of a reaction mixture containing acetone peroxides

From the synthesis of phenol by oxidation of cumene, a crude oxidate containing, after concentration, essentially cumenyl hydroperoxide (CHPO) and 2-phenyl-2-propanol was obtained.

This crude oxidate was subjected to a procedure for the acid splitting of the CHPO to phenol and acetone, after having added the necessary amount of a 70% by weight aqueous solution of $H_2O_2$ to oxidize the 2-phenyl-2-propanol to CHPO.

The splitting of the CHPO was carried out by simultaneous injection of the oxidate and concentrated sulfuric acid into a stainless steel reactor provided with an overflow pipe.

The reactor in which this acid splitting operation was carried out was provided with a cooling jacket associated with a thermostatted bath, in order to allow removal of the heat evolved by the reaction.

Splitting conditions (i) $H_2O_2$:2-phenyl-2-propanol molar ratio = 1;
(ii) $H_2SO_4$:crude oxidate weight ratio = 1.25%;
(iii) Temperature maintained at 57° C.;
(iv) Mean residence time in the reactor = 7.4 minutes.

The final oxidate was analyzed by gas phase chromatography.

Other than principal final products (phenol and acetone), the following were determined:

(I) Dimeric acetone peroxide : 0.4200% by weight (detection limit: 0.0020%);
(II) Trimeric acetone peroxide : 0.0400% by weight (detection limit: about 0.0100%).

EXAMPLE 2

Destruction of the acetone peroxides in the oxidate prepared in Example 1

20 g of the final oxidate produced in Example 1 were charged into a pressure-resistant 30 $cm^3$ glass flask provided with a reflux condenser.

The mixture was heated to 57° C. for 30 minutes, then cooled and the mixture was neutralized to pH 5.6 (as defined herein) using a 7.7 N caustic soda solution.

0.014 g of cupric acetate (0.1134 mmol) was then added.

The mixture was heated with stirring to 110° C. for 20 minutes, under autogenous pressure.

By gas phase chromatography (GC) measurement, the total disappearance of the dimeric acetone peroxide and the trimeric acetone peroxide (within the above-mentioned detection limits of the measurement) were determined.

EXAMPLE 3

Destruction of the acetone peroxides in the oxidate prepared in Example 1

The procedure of Example 2 was repeated, modifying the heating phase after adjustment of the pH to 5.7 and the addition of cupric acetate; the mixture was heated, with stirring and under autogenous pressure, for 1 hour, 45 minutes, to 73° C.

The total disappearance (within the above-mentioned detection limits) of the dimeric acetone peroxide and the trimeric acetone peroxide were determined by GC measurement.

EXAMPLE 4

Destruction of the acetone peroxides in the oxidate prepared in Example 1

20 g of the final oxidate produced in Example 1 were charged into a pressure-resistant 30 cm³ glass flask.

Concentrated (7.7 N) caustic soda was added until pH 5.8 (measured under the conditions described above) was reached.

The sodium sulfate formed was filtered off, and 0.01 g (0.1134 mmol) of copper acetate was added.

The mixture was heated with stirring for 1 hour, 30 minutes, to 110° C., under autogenous pressure.

The total disappearance (within the detection limits indicated above) of the dimeric acetone peroxide and the trimeric acetone peroxide was determined by GC measurement.

Comparative Experiment A

The procedure of Example 2 was repeated, but the copper acetate was charged into the oxidate at the beginning of the experiment, and the pH value (1.6) was not adjusted.

The mixture was heated with stirring and under autogenous pressure for 1 hour at 57° C.

By GC measurement, the following were determined in the final reaction mixture:

(I) 0.3990% of dimeric acetone peroxide (about 95% of the amount present before treatment);

(II) the trimeric acetone peroxide had disappeared (within the detection limits indicated above).

EXAMPLE 5

Preparation of a reaction mixture containing acetone peroxides

The following materials were charged into a 3-necked 500 cm³ glass flask, provided with a central stirrer and a dropping funnel:

(i) 100 g (1.064 mol) of phenol;
(ii) 78 g of acetone;
(iii) 5 g of a titanium silicalite (prepared according to French Patent FR 2,471,950) having a $TiO_2:SiO_2$ molar ratio of about 3%.

The mixture was stirred and heated to 80° C., then 20 cm³ of a 36% (weight/volume) aqueous solution of $H_2O_2$ (0.2 mol) were introduced.

When the $H_2O_2$ had been consumed, the catalyst was separated by filtration and the following were determined in reaction mixture 5A, as well as the major compounds (untransformed phenol, acetone, diphenols) by gas phase chromatography (GC):

(I) 0.0065% by weight of dimeric acetone peroxide;
(II) 0.0200% by weight of trimeric acetone peroxide.

The catalyst used above was recovered and used in two successive new hydroxylations of phenol.

In these two experiments, 5B and 5C, the acetone peroxides were measured by GC.

Experiment 5B (I) Dimeric acetone peroxide 0.0170% by weight;
(II) Trimeric acetone peroxide 0.0250% by weight.

Experiment 5C (I) Dimeric acetone peroxide 0.0340% by weight;
(II) Trimeric acetone peroxide 0.0650% by weight.

EXAMPLE 6

18 0 g of reaction mixture 5C prepared in Example 5 were charged into the apparatus described in Example 2.

The pH (measured under the conditions described above) was adjusted to a value of 5.2.

0.028 g of copper acetate was then added and the mixture was heated to 110° C. for 1 hour under autogenous pressure.

The total disappearance (within the detection limits indicated above) of the dimeric acetone peroxide and the trimeric acetone peroxide was determined by GC measurement.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the destruction of the acetone peroxides present in an oxidate reaction mixture comprising (a) adjusting the pH of said reaction mixture to a value ranging from 4 to 8; (b) adding an effective amount of a copper compound to said reaction mixture; and (c) maintaining such reaction mixture at a temperature ranging from 50° C. to 150° C.

2. The process as defined by claim 1, said copper compound comprising a cuprous or cupric compound that is at least partially soluble in said reaction mixture.

3. The process as defined by claim 1, said copper compound comprising a cupric carboxylate, cupric halide, copper sulfate or copper nitrate.

4. The process as defined by claim 3, said copper compound comprising cupric acetate.

5. The process as defined by claim 1, comprising adding from 0.05 mole to 5 moles of copper compound per mole of acetone peroxide 6. The process as defined by claim 5, comprising adding from 0.1 mole to 2 moles of copper compound per mole of acetone peroxide.

7. The process as defined by claim 1, comprising adjusting the pH of the reaction mixture to a value ranging from 5 to 7.

8. The process as defined by claim 1, carried out at a temperature ranging from 60° C. to 130° C.

9. The process as defined by claim 1, comprising first adjusting the pH of the reaction mixture, next adding the copper compound thereto, and then adjusting the temperature of the reaction mixture to from 50° to 150° C.

10. The process as defined by claim 1, comprising heating the reaction mixture for a few minutes to a few hours at a pH of less than 4, in the presence or absence of the copper compound, next adjusting the pH of the reaction mixture to a value ranging from 4 to 8 after cooling, adding the copper compound if required, and resuming heating the reaction mixture to the same or to a higher temperature than above.

11. The process as defined by claim 1, said reaction mixture comprising the oxidate from the synthesis of a phenol, diphenol, or derivative thereof.

12. The process as defined by claim 11, said reaction mixture comprising a cumene oxidate 13. The process as defined by claim 11, said reaction mixture comprising a 1,4-diisopropylbenzene oxidate.

14. The process as defined by claim 1, said reaction mixture comprising the oxidate from the hydroxylation of a phenol, diphenol or derivative thereof.

15. The process as defined by claim 1, carried out in a closed reactor.

* * * * *